United States Patent
James et al.

(10) Patent No.: US 9,730,859 B2
(45) Date of Patent: Aug. 15, 2017

(54) TAMPER-EVIDENT INDICATOR FOR A DRUG RESERVOIR

(75) Inventors: Aled Meredydd James, Shirley (GB); James Andrew Holt, Leamington Spa (GB); Richard James Vincent Avery, Mickleton (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 520 days.

(21) Appl. No.: 13/989,879

(22) PCT Filed: Dec. 7, 2011

(86) PCT No.: PCT/EP2011/072137
§ 371 (c)(1),
(2), (4) Date: Jun. 28, 2013

(87) PCT Pub. No.: WO2012/076626
PCT Pub. Date: Jun. 14, 2012

(65) Prior Publication Data
US 2013/0281962 A1 Oct. 24, 2013

Related U.S. Application Data

(60) Provisional application No. 61/420,839, filed on Dec. 8, 2010.

(30) Foreign Application Priority Data

Feb. 4, 2011 (EP) ..................................... 11153431

(51) Int. Cl.
*A61J 1/06* (2006.01)
*A61M 5/24* (2006.01)
*A61M 5/50* (2006.01)

(52) U.S. Cl.
CPC .................. *A61J 1/06* (2013.01); *A61M 5/24* (2013.01); *A61M 5/2455* (2013.01); *A61M 5/50* (2013.01); *A61M 5/5086* (2013.01)

(58) Field of Classification Search
CPC .......... A61J 1/06; A61M 5/2455; A61M 5/50; A61M 5/5086
See application file for complete search history.

(56) References Cited

U.S. PATENT DOCUMENTS

| 4,465,200 A | 8/1984 | Percarpio |
| 4,667,837 A | 5/1987 | Vitello et al. |

(Continued)

FOREIGN PATENT DOCUMENTS

| DE | 3618158 | 12/1987 |
| DE | 19925621 A1 | 12/1999 |

(Continued)

OTHER PUBLICATIONS

International Search Report for Int. App. No. PCT/EP2011/072137, completed Mar. 9, 2012.

(Continued)

*Primary Examiner* — Leslie Deak
*Assistant Examiner* — Kai Weng
(74) *Attorney, Agent, or Firm* — McDonnell Boehnen Hulbert & Berghoff LLP

(57) ABSTRACT

A drug reservoir comprises of a housing having a proximal end and a distal end, wherein the housing is configured to hold a medicament; and a removable feature disposed on at least one of the proximal end and the distal end, wherein the removable feature covers at least in part one of the proximal end and the distal end.

6 Claims, 4 Drawing Sheets

(56) References Cited

U.S. PATENT DOCUMENTS

| | | | |
|---|---|---|---|
| 5,464,111 A | 11/1995 | Vacek et al. | |
| 5,807,323 A | 9/1998 | Kriesel et al. | |
| 6,126,640 A | 10/2000 | Tucker et al. | |
| 2008/0097310 A1* | 4/2008 | Buehler | A61M 5/50 604/111 |

FOREIGN PATENT DOCUMENTS

| | | |
|---|---|---|
| JP | H10-155904 A | 6/1998 |
| JP | 2001-513683 A | 9/2001 |
| JP | 2004-538118 A | 12/2004 |
| JP | 2005-192888 A | 7/2005 |
| JP | 2006-034790 A | 2/2006 |
| JP | 2007-216986 A | 8/2007 |
| JP | 2007-216987 A | 8/2007 |
| JP | 2009-240411 A | 10/2009 |
| JP | 2010-509963 A | 4/2010 |
| WO | 98/37855 | 9/1998 |
| WO | 99/65549 | 12/1999 |
| WO | 03/017915 A1 | 3/2003 |
| WO | 2008/059063 | 5/2008 |

OTHER PUBLICATIONS

International Search Report and Written Opinion for Int. App. No. PCT/EP2011/072137 mailed Mar. 22, 2012.
Japanese Office Action for JP Application No. 2013-542532, mailed Nov. 17, 2015.

\* cited by examiner

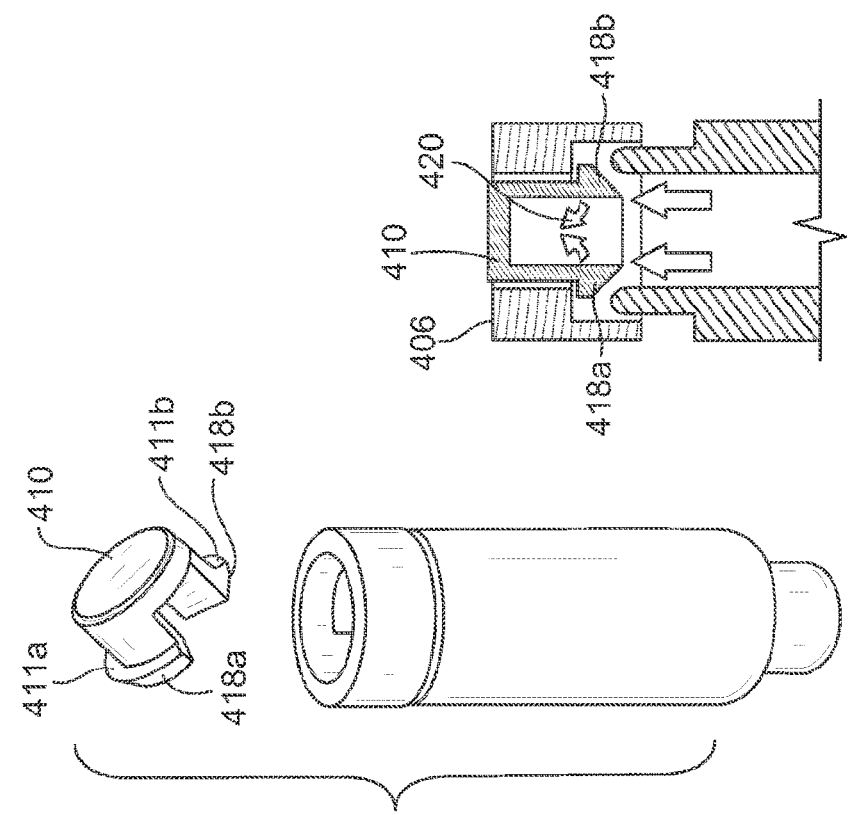
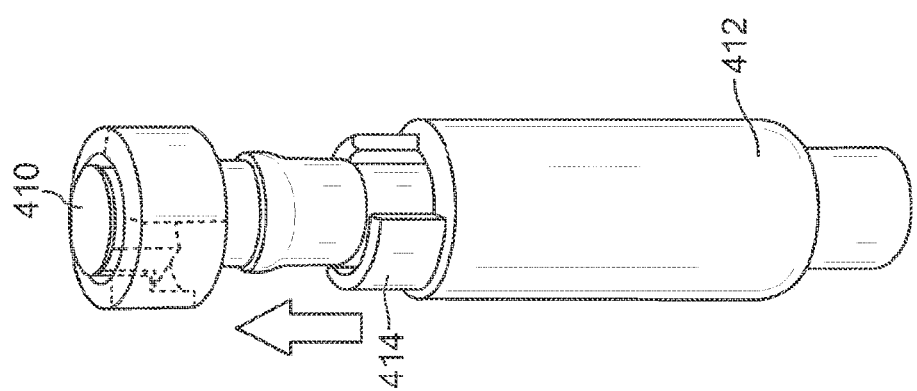
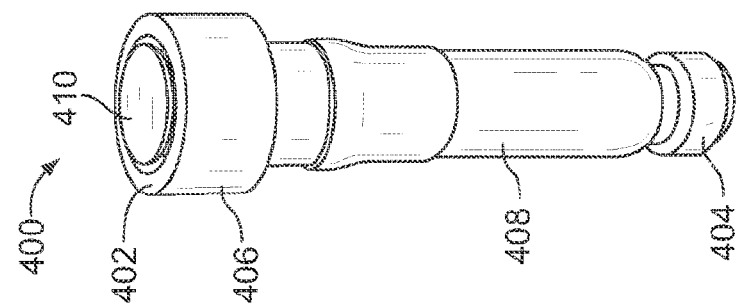

TAMPER-EVIDENT INDICATOR FOR A DRUG RESERVOIR

CROSS REFERENCE TO RELATED APPLICATIONS

The present application is a U.S. National Phase Application pursuant to 35 U.S.C. §371 of International Application No. PCT/EP2011/072137 filed Dec. 7, 2011, which claims priority to U.S. Provisional Patent Application No. 61/420,839 filed Dec. 8, 2010 and European Patent Application No. 11153431.9 filed Feb. 4, 2011. The entire disclosure contents of these applications are herewith incorporated by reference into the present application.

FIELD OF DISCLOSURE

The present disclosure is generally directed to drug delivery devices and reservoirs, particularly reservoirs containing a medicament. More particularly, the present disclosure is generally directed to a tamper-evident indicator for a drug reservoir. As just one example, such medicament reservoirs may comprise an ampoule, a cartridge, a vial, or a pouch, and may be used with a medical delivery device. Exemplary medical delivery devices include, but are not limited to syringes, pen type injection syringes, pumps, inhalers, or other similar injection or infusing devices that require at least one reservoir containing at least one medicament.

BACKGROUND

Medicament reservoirs such as ampoules, cartridges, or vials are generally known. Such reservoirs are especially used for medicaments that may be self administered by a patient. For example, with respect to insulin, a patient suffering from diabetes may require a certain amount of insulin to either be injected via a pen type injection syringe or infused via a pump. With respect to certain known reusable pen type drug delivery devices, a patient loads a cartridge containing the insulin into a proximal end of a cartridge holder. After the cartridge has been correctly loaded, the user may then be called upon to select a dose of medicament. Multiple doses may be dosed from the cartridge. Where the drug delivery device comprises a reusable device, once the cartridge is empty, the cartridge holder is disconnected from the drug delivery device and the empty cartridge is removed and replaced with a new cartridge. Most suppliers of such cartridges recommend that the user dispose of the empty cartridges properly. Where the drug delivery device comprises a disposable device, once the cartridge is empty, the user is recommended to dispose of the entire device.

Such known self administration systems requiring the removal and reloading of empty cartridges have certain limitations. For example, in certain generally known systems, a user simply loads a new cartridge into the delivery system without the drug delivery device or without the cartridge having a mechanism of preventing cross use of an incorrect cartridge. That is, the drug delivery device does not have a mechanism for determining if the medicament contained in the cartridge is indeed the correct type of medicament to be administered by the patient. Alternatively, certain known drug delivery devices do not present a mechanism for determining if the correct type of medicament within the cartridge should be used with that particular drug delivery system. This potential problem could be exacerbated given that certain elderly patients, such as those suffering from diabetes, may have limited manual dexterity. Identifying an incorrect medicament is quite important, since the administration of a potentially incorrect dose of a medicament such as a short acting insulin in lieu of a long insulin could result in injury or even death.

Some drug delivery devices or systems may use a color coding scheme to assist a user or care giver in selecting the correct cartridge to be used with a drug delivery device. However, such color coding schemes pose challenges to certain users, especially those users suffering from poor eyesight or color blindness: a situation that can be quite prevalent in patients suffering from diabetes.

Another concern that may arise with such disposable cartridges is that these cartridges are manufactured in essentially standard sizes and manufactured to comply with certain recognized local and international standards. Consequently, such cartridges are typically supplied in standard sized cartridges (e.g., 3 ml cartridges). Therefore, there may be a variety of cartridges supplied by a number of different suppliers and containing a different medicament but they may fit a single drug delivery device. As just one example, a first cartridge containing a first medicament from a first supplier may fit a medical delivery device provided by a second supplier. As such, a user might be able to load and then dispense an incorrect medicament (such as a rapid or basal type of insulin) into a drug delivery device without being aware that the medical delivery device was perhaps neither designed nor intended to be used with such a cartridge.

As such, there is a growing desire from users, health care providers, care givers, regulatory entities, and medical device suppliers to reduce the potential risk of a user loading an incorrect drug type into a drug delivery device. There is also, therefore, a desire to reduce the risk of dispensing an incorrect medicament (or the wrong concentration of the medicament) from such a drug delivery device.

There is, therefore, a general need to physically dedicate or mechanically code a cartridge to its drug type and design an injection device that accepts or works with the dedication or coded features provided on or with the cartridge so as to prevent unwanted cartridge cross use. Similarly, there is also a general need for a dedicated cartridge that allows the medical delivery device to be used with an authorized cartridge containing a specific medicament while also preventing undesired cartridge cross use.

There is also a general need to provide a dedicated cartridge that is difficult to tamper with so that the cartridge may not be compromised in that the cartridge can be used with an unauthorized drug or drug delivery device. Because such cartridges may be difficult to tamper with, they may also reduce the risk of counterfeiting: i.e., making it more difficult for counterfeiters to provide unregulated counterfeit medicament carrying products. It is an aim to provide an improved drug reservoir.

SUMMARY

This aim can be achieved by a drug reservoir according to claim 1. The drug reservoir comprises a housing having a proximal end and a distal end, wherein the housing is configured to hold a medicament. A removable feature is disposed on at least one of the proximal end and the distal end, wherein the removable feature covers at least in part one of the proximal end and the distal end.

Another drug reservoir arrangement comprises a housing having a proximal end and distal end and a removable feature, for example a tear-away feature, disposed on at least one of the proximal and distal end, wherein the removable feature covers the at least one of the proximal end and distal end.

According to an exemplary arrangement, a drug reservoir has a tamper-evident indicator. The drug reservoir includes a housing having a proximal end and a distal end, where the housing is configured to hold a medicament. The drug reservoir further includes a removable feature disposed on at least one of the proximal end and the distal end, where the removable feature covers at least in part one of the proximal end and the distal end.

According to an exemplary arrangement, a drug reservoir includes a reservoir body having a proximal end and a distal end, wherein the reservoir body holds a medicament. The drug reservoir also includes a removable feature, for example a tear-away feature disposed on the reservoir body, wherein the tear-away feature acts as a tamper-evident indicator or feature, and wherein the tear-away feature at least partially covers at least one of a warning feature, a fastening feature, and a coding feature. The tear-away feature may be located on the proximal end or on the distal end. The tear-away feature may be a tear-away label or a tear away strip. In one embodiment the tamper-evident feature or tear-away feature comprises at least one of foil, vinyl, polyester, and acetate.

The distal end of one embodiment comprises an opening and a septum, wherein the tear-away feature covers the opening and the septum.

One embodiment of the drug reservoir comprises a colored element, wherein the tamper-evident or tear-away feature covers the colored element, and wherein the colored element comprises a color that serves to indicate information about the drug reservoir.

Another embodiment of the drug reservoir comprises a fastening feature, wherein the tamper-evident feature or tear-away feature is disposed over the fastening feature.

One embodiment of the drug reservoir comprises a coding feature, wherein the coding feature is complementary to a corresponding coding feature of a given reservoir holder intended for use with the drug reservoir, and wherein the tamper-evident or tear-away feature covers the coding feature. One embodiment of the drug reservoir comprises a coding feature, wherein the coding feature is complementary to a corresponding coding feature of a given drug delivery device intended for use with the drug reservoir, and wherein the tamper-evident or tear-away feature covers the coding feature.

In one embodiment the tear-away feature comprises a three-dimensional coding feature, and wherein at least a portion of the three-dimensional coding feature is removed when the tear-away feature is removed from the drug reservoir.

The drug reservoir may comprise a cap element, and wherein, when a user tears the tear-away feature, the cap-element is removed.

One embodiment of the drug reservoir comprises a cartridge bung, wherein the bung is located in the housing, and wherein the tear-away feature prevents access to the cartridge bung. In one embodiment the tear-away feature prevents attachment of a dispense interface to the drug reservoir distal end, e.g. the cartridge distal end.

One embodiment of the drug reservoir includes one of an ampoule, a cartridge, a vial, or a pouch.

According to another exemplary arrangement the drug reservoir further comprises a collar on the proximal end; wherein the removable feature is a plug feature that is disposed at least partially in the collar, wherein the plug feature is configured such that the plug feature is automatically removed when the drug reservoir is inserted in a corresponding reservoir holder.

In one embodiment the drug reservoir comprises a collar on the proximal end; wherein the removable feature is a plug feature that is disposed at least partially in the collar, wherein the plug is configured such that the plug is automatically removed when the cartridge is inserted in a corresponding drug cartridge holder.

In another arrangement, a drug cartridge includes a housing having a proximal end and distal end, a collar on the proximal end, and a plug feature disposed at least partially in the collar. The plug is configured such that the plug is automatically removed when the cartridge is inserted in a corresponding drug cartridge holder.

In a further arrangement, the removable feature is a plug feature that is disposed at least partially in the collar. The plug is configured such that the plug is automatically removed when the cartridge is inserted in a corresponding drug cartridge holder.

One embodiment comprises a cartridge bung, wherein the bung is located in the housing, and wherein the plug feature prevents access to the cartridge bung.

One embodiment of the plug feature comprises at least two flexible arms, wherein the flexible arms bend inward when the reservoir is inserted in a corresponding drug cartridge holder. Each of the at least two flexible arms may comprise an angled protrusion, and wherein each angled protrusion hooks the plug feature to the collar.

In one embodiment a feature on the corresponding cartridge holder forces the flexible arms to bend inward as the drug reservoir is inserted in the cartridge holder. After the flexible arms are bent a given amount, the angled protrusions no longer hook the plug feature to the collar.

These as well as other advantages of various aspects of the present invention will become apparent to those of ordinary skill in the art by reading the following detailed description, with appropriate reference to the accompanying drawings.

The scope of the invention is defined by the content of the claims. The invention is not limited to specific embodiments but comprises any combination of elements of different embodiments. Moreover, the invention comprises any combination of claims and any combination of features disclosed by the claims.

BRIEF DESCRIPTION OF THE DRAWINGS

Exemplary embodiments are described herein with reference to the drawings, in which:

FIG. 4A is a perspective view of an example drug reservoir in accordance with an embodiment of the proposed concept;

FIG. 4B is a perspective view of the examplary embodiment of the drug reservoir of FIG. 4A as it is inserted in an examplary embodiment of a reservoir holder;

FIG. 4C is a perspective view of the the examplary embodiment of the drug reservoir of FIG. 4A fully inserted in the examplary embodiment of the reservoir holder of FIG. 4B;

FIG. 4D is a cross-sectional view of a proximal end of the examplary embodiment of the drug reservoir of FIG. 4A as it is inserted in the examplary embodiment of the reservoir holder of FIG. 4B;

DETAILED DESCRIPTION

Figure 1A:
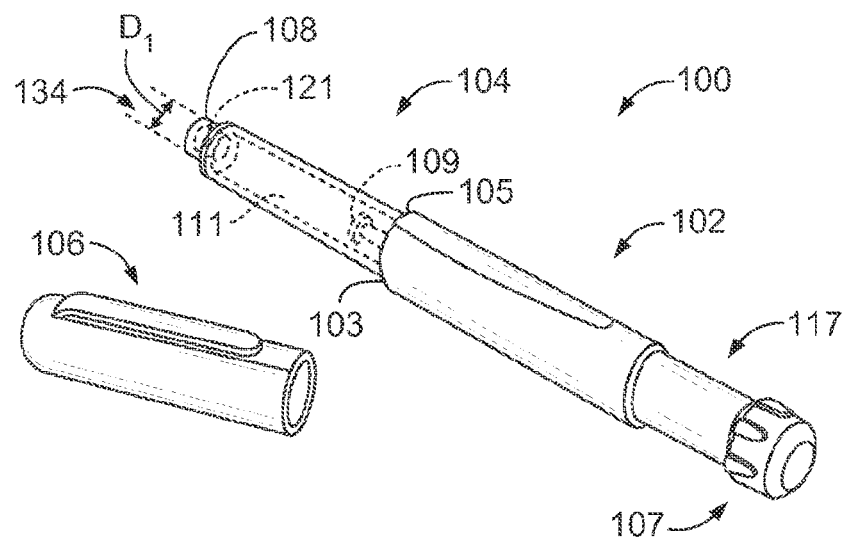
FIG. 1A illustrates an exemplary embodiment of a pen type drug delivery device.

The terms "medicament" or "drug", as used herein, preferably mean a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;

or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

FIG. 1A illustrates a drug delivery device 100 in the form of a pen type syringe. This drug delivery device 100 comprises a dose setting mechanism 102, a cartridge holder 104, and a removable cap 106. A proximal end 105 of the cartridge holder 104 and a distal end 103 of the dose setting mechanism 102 are removably secured together. The pen type syringe may comprise a re-usable or a disposable pen type syringe. Where the syringe comprises a reusable device, the cartridge holder 104 and the dose setting mechanism 102 are removably coupled together. In a disposable device, they may be permanently coupled together. In FIG. 1A, the dose setting mechanism 102 comprises a spindle 109, such as a threaded spindle that rotates when a dose is injected.

To inject a previously set dose, a double ended needle assembly (not shown) is attached to a distal end 108 of the cartridge holder 104. Preferably, the distal end 108 of the cartridge holder 104 comprises a thread 121 (or other suitable connecting mechanism such as a snap lock, snap fit, form fit, or bayonet lock mechanism) so that the needle assembly may be removably attached to the distal end 108 of the cartridge holder 104. When the drug delivery device 100 is not in use, the removable cap 106 can be releasably retained over the cartridge holder 104.

Figure 1B:
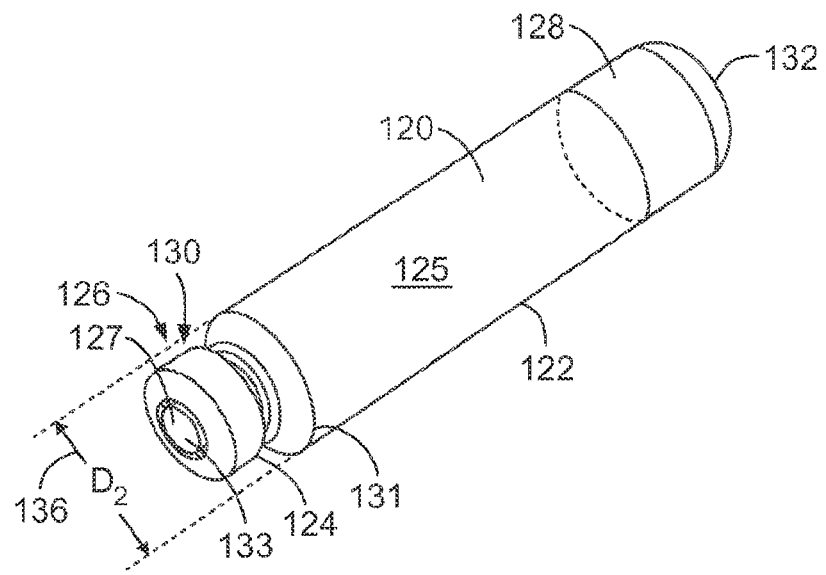
FIG. 1B illustrates an exemplary embodiment of a drug cartridge.

An inner cartridge cavity 111 defined by the cartridge holder 104 is dimensioned and configured to securely receive and retain the cartridge 120. FIG. 1B illustrates a perspective view of the cartridge 120 that may be used with the drug delivery device 100 illustrated in FIG. 1A. The cartridge 120 includes a generally tubular barrel 122 extending from a distal end 130 to a proximal end 132. The distal end 130 is defined by an inwardly converging shoulder 131.

At the distal end 130, the cartridge 120 includes a smaller diameter neck 126 and this neck 126 projects distally from the shoulder 131 of the barrel 122. Preferably, this smaller diameter neck 126 is provided with a large diameter annular bead 133 and this bead 133 extends circumferentially thereabout at the extreme distal end of the neck 126. A pierceable seal or septum 127 is securely mounted across the open distal end 130 defined by the neck 126. The seal 127 may be held in place by a metallic sleeve or ferrule 124. This ferrule 124 may be crimped around the circumferential bead 133 at the distal end of the neck 126. The medicament 125 is pre-filled into the cartridge 120 and is retained within the cartridge 120, in part, by the pierceable seal 127, the metallic sleeve or ferrule 124, and the bung or the stopper 128. The stopper 128 is in sliding fluid-tight engagement with the inner tubular wall of the barrel 122. Axially directed forces acting upon the bung or the stopper 128 during dose injection or dose administration urges the medicament 125 from the cartridge 120 though a double ended needle mounted onto the distal end 108 of the cartridge holder 104 and into the injection site. Such axial forces may be provided by the spindle 109.

A portion of the cartridge holder 104 defining the cartridge holder cavity 111 is of substantially uniform diameter represented in FIG. 1A by $D_1$ 134. This diameter $D_1$ 134 is preferably slightly greater than the diameter $D_2$ 136 of the cartridge 120. The interior of the cartridge holder 104 includes an inwardly-extending annular portion or stop that is dimensioned to prevent the cartridge 120 from moving within the cartridge holder 104. In this manner, when the cartridge 120 is loaded into the cavity 111 of the cartridge holder 104 and the cartridge holder 104 is then connected to the dose setting member 102, the cartridge 120 will be securely held within the cartridge cavity 111. More particularly, the neck 126 and ferrule 124 of the cartridge 120 are inserted in a proximal to distal direction into the open proximal end 105 of the cartridge holder 104 with the ferrule 124 eventually passing entirely into the holder 104. With the holder 104 removably coupled to the dose setting mechanism 102, the proximal end 132 of the cartridge 120 will typically abut a stop provided by the dose setting member 102.

A number of doses of a medicament 125 may be dispensed from the cartridge 120. It will be understood that the cartridge 120 may contain a type of medicament 125 that must be administered often, such as one or more times a day. One such medicament 125 is insulin. A movable piston or stopper 128 is retained in a first end or proximal end 132 of the cartridge 120 and receives an axial force created by the spindle 109 of the dose setting mechanism 102.

The dose setting mechanism 102 comprises a dose setter 117 at the proximal 107 end of the dose setting mechanism 102. In one preferred arrangement, the dose setter 117 may extend along the entire length of the dose setting mechanism 102. The dose setter 117 may be rotated by a user so as to set a dose.

To administer a dose that may be set by rotating the dose setter 117, the user attaches the needle assembly comprising a double ended needle on the distal end 108 of the cartridge holder 104. In this manner, the needle assembly pierces the seal 127 of the cartridge 120 and is therefore in liquid communication with the medicament 125. The user pushes on the dose setter 117 to inject the set dose. The same dose setting and dose administration procedure is followed until the medicament 125 in the cartridge 120 is expended and then a new cartridge 120 must be loaded in the drug delivery device 100. To exchange an empty cartridge 120, the user is called upon to remove the cartridge holder 104 from the dose setting mechanism 102.

Generally, a tamper-evident indicator for a drug reservoir or drug reservoir assembly (e.g., a cartridge holder 104 holding a cartridge 120, or a molded drug cartridge) is provided. The tamper-evident feature may indicate to a user whether the drug reservoir has been tampered with. For example, the tamper-evident feature may beneficially indicate to a user of the reservoir that that reservoir has been previously opened. In addition, the tamper-evident feature may beneficially serve to indicate whether the drug is an appropriate drug for a given drug delivery system 100. In an example, a user may need to remove the tamper-evident feature from the drug reservoir before the drug reservoir can be used in a drug delivery system 100 for a first time. Further, the tamper-evident feature may reveal, incorporate, or remove a mechanical coding feature(s), so that the drug reservoir can only be inserted or connected to a holder 104 and/or drug delivery device 100 if the coding feature is correct.

Figure 2:
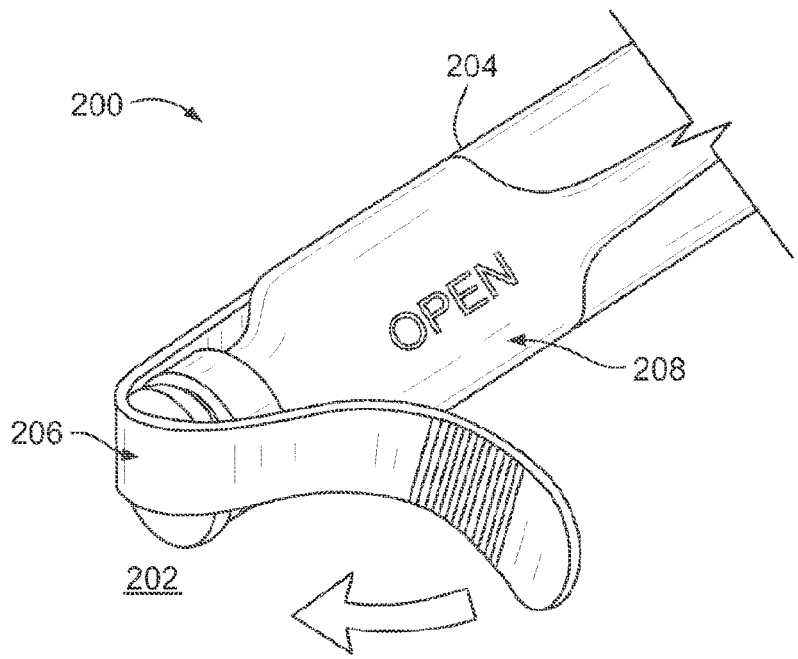
FIG. 2 is a perspective view of a distal end of an embodiment of a drug reservoir having an example tear-away feature that serves as a tamper-evident indicator.

In a first embodiment, a drug reservoir includes a reservoir body 204 (in FIG. 2) having a proximal end and a distal end 202 and a removable feature disposed on the reservoir body, where the removable feature is a tear-away feature 206 (in FIG. 2). The tear-away 206 feature acts as a tamper-evident indicator and at least partially covers at least one of a warning feature 208 (in FIG. 2), a fastening feature, or a coding feature.

FIG. 2 depicts an example drug reservoir having a tear-away feature 206 that serves as a tamper-evident indicator. Specifically, FIG. 2 depicts a distal end 202 of drug cartridge 200. Drug cartridge 200 includes a body 204, which holds a medicament 125, such as insulin. Tear-away feature 206 is disposed near the distal end 202 on the body 204 and, prior to being removed by a user, covers a warning feature 208. In this particular example, the tear-away feature 206 comprises a tear-away strip that extends over a septum 127 of the drug cartridge 200. Therefore, the tear-away feature 206 prevents access to a septum 127 near the distal end of the drug cartridge 200, and therefore the medicament 125, until the tear-away feature 206 is removed or tampered with in some other way.

In some embodiments, the tear-away feature 206 may act as a label. Further, the tear-away feature 206 may be manufactured of materials that are known to show evidence of tampering, such as foil, vinyl, polyester, or acetate.

Returning to FIG. 2, the warning feature 208 that the tamper-evident feature or tear-away feature 206 covers is the word "OPEN". Such a warning may indicate to a user that the cartridge 200 has previously been opened or used. Other warning features 208 are possible as well. For instance, a possible warning feature 208 is text that indicates the type of drug and explains warnings related specifically to that type of drug.

In an example, removal of the tamper-evident indicator may reveal the color of underlying components. The color may serve to indicate information about the drug reservoir. For example, the color may serve to highlight the choice of drug to the user. In another example of the proposed concept, the removal of a tear-away feature 206 may reveal additional features, such as fastening features or coding features 308 (in FIG. 3). Generally, a coding feature 308 may be any feature that is configured to pass into or through a corresponding coding feature provided by a reservoir holder of a drug delivery device 100. Alternatively, if the tear-away feature 206 is disposed on a cartridge assembly, such as a molded cartridge, the coding feature 308 may be any feature that is configured to pass into or through a corresponding coding feature provided by the drug delivery device 100. Many different coding features 308 are possible. In an example, a coding feature 308 may include one or more protrusions 308a, 308b, 308c (in FIG. 3), and the corresponding coding feature of the reservoir holder may include an indentation or indentations to accommodate the one or more protrusions 308a, 308b, 308c; however, vice versa is also possible. That is, the coding feature 308 may include one or more indentations, and the corresponding coding feature of the reservoir holder may include a protrusion or protrusions coded to the one or more indentations. Still alternatively, the coding feature 308 may include both at least one protrusion 308a, 308b, 308c and at least one indentation.

Generally, any type of coding features 308 may be incorporated into the cartridge 300 and the corresponding holder coding feature. For instance, the coding features 308 may include a plurality of code elements (e.g., protrusions). In addition, the coding feature elements may vary in size, cross-sectional shape, and position. For example, the axial extent, circumferential extent, radial extent, cross-section shape (in any plane, e.g., longitudinal or traverse) of the protrusions 308a, 308b, 308c may be varied. The size of each protrusion 308a, 308b, 308c may be different from the others. For example, there may be a number of different protrusions 308a, 308b, 308c with different radial extents. Regarding varying the cross-section shape, a coding system may consist of a number of coding features 308, each of which is smaller in one area and larger in another than all of the other coding features 308 of the coding system.

It should be appreciated from the above that a large number of coding schemes are possible, and a large number of cartridges may easily be distinguished from one another. The tear-away feature 206 may cover these coding features 308 or fastening features. As such, without removal of the tear-away feature 206, fastening or coding of the reservoir or assembly may not be able to be achieved. Therefore, a user may need to remove the tear-away label 302 (in FIG. 3) before the reservoir may be used with a drug delivery device 100. Further, as mentioned above, the tear-away feature 206 covers the coding and beneficially acts as an indicator of possible tampering.

Figure 3:
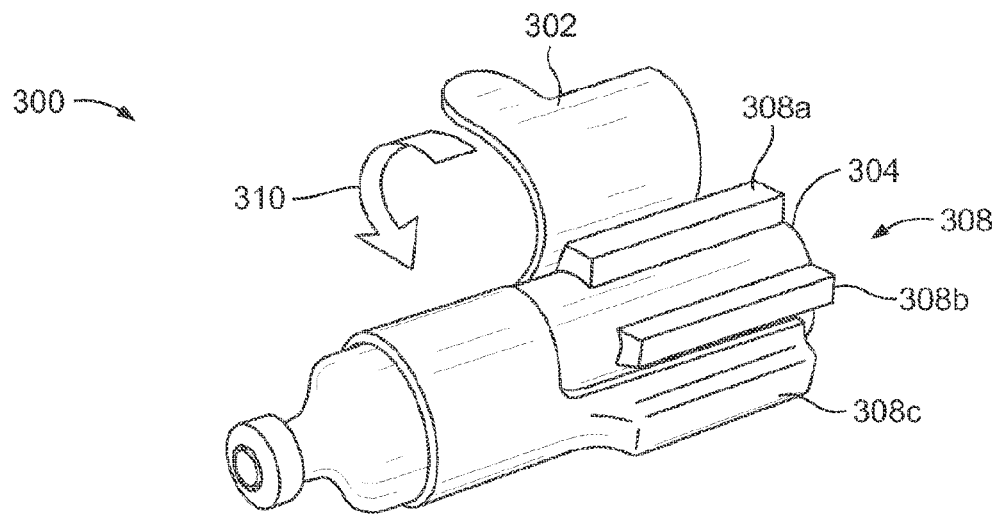
FIG. 3 is a perspective view of an examplary embodiment of a drug reservoir having an example tear-away feature that serves as a tamper-evident indicator.

FIG. 3 depicts another example drug reservoir having an example tear-away feature that serves as a tamper-evident indicator and covers a coding feature 308 of the drug reservoir. Cartridge 300 includes a tear-away label 302 disposed on the proximal end 304 of the cartridge 300. Prior to being removed by a user, the tear-away label 302 covers coding feature 308, which includes protrusions 308a, 308b, 308c. As can be seen, the tear-away label 302 may be configured to be removed by a user by the user pulling the feature or tear-away label 302 in direction 310.

In another example, the tear-away feature could be configured such that removal of the tear-away feature removes given coding features of elements from the device. Before the given coding features are removed, the coding features may prevent assembly of the cartridge 300 into its holder.

In another embodiment of the proposed disclosure, the tamper-evident indicator may take the form of a collar 406 (in FIG. 4) with a removable feature (e.g., a plug 410) that is automatically removed when a reservoir is inserted into a reservoir holder. Generally, a drug cartridge 400 (in FIG. 4) may include a housing having a proximal end and distal end, a collar 406 on the proximal end, and a plug feature 410 disposed at least partially in the collar 406. The plug 410 is configured such that the plug 410 is automatically removed when the cartridge 400 is inserted in a corresponding drug cartridge holder 412 (in FIG. 4). An example operation of such a tamper-evident indicator is shown in FIGS. 4A-D.

Cartridge 400 includes a proximal end 402 and a distal end 404. A collar 406 is located at proximal end 404, and this collar 406 has a width that is greater than body 408 of the cartridge 400. A plug feature 410 is disposed at least partially in collar 406. The plug 410 is configured such that the plug 410 is automatically removed when the cartridge 400 is inserted in a corresponding drug cartridge holder, such as cartridge holder 412. For example, as shown in FIGS. 4B-C, the plug feature 410 is ejected from the collar 402 when the cartridge 400 is fully inserted into cartridge holder 412.

In an example, the plug feature 410 comprises at least two flexible arms 411a, 411b, wherein the flexible arms 411a, 411b bend inward when the cartridge 400 is inserted in a corresponding drug cartridge holder 412. For instance, as shown in FIG. 4C, plug feature 410 includes two flexible arms 411a and 411b. The flexible arm 411a includes an angled protrusion 418a and flexible arm 411b includes an angled protrusion 418b. As seen in FIG. 4D, these angled protrusions 418a, 418b hook the plug feature 410 to the collar 406.

In order to force the plug 410 to eject from the collar 406, the holder 412 may include a feature 414 for removing the plug feature 410, e.g. protrusions, that forces the flexible arms 411a, 411b to bend inward as the drug reservoir or cartridge 400 is inserted in the cartridge holder 412. For instance, the holder 412 may have a feature 414 on the proximal end that is configured to interact with the plug feature 410 and force the plug feature 410 from the collar 406 when the cartridge 400 is attached to the holder 412. Feature 414 forces the flexible arms 411a, 411b to bend inward (specifically in direction 420 indicated in FIG. 4D) as the drug reservoir or cartridge 400 is inserted in the cartridge holder 412. After the flexible arms 411a, 411b are bent a given amount, the angled protrusions 418a, 418b no longer hook the plug feature 410 to the collar 406, and the plug 410 can be forced in the proximal direction out of the collar 406, as shown in FIG. 4C.

The drug cartridge 400 may include a cartridge bung (not shown) in the housing, and the plug feature 410 prevents access to the cartridge bung before the plug 410 is removed. Therefore, the cartridge 400 may not be used before it is inserted in a correct drug delivery device 100. Mechanical coding features may prevent use of cartridge 400 with an incorrect holder 412. In the example of FIG. 4B, collar 406 includes indentations into which the coding protrusions 414 can pass, the protrusions or features 414 for removing the plug feature 410 being configured to interact with the plug feature 410.

It should be understood that different drug cartridges 400 holding different medicaments 125 may include plug features 410 of various shapes, sizes, and types. Further, various reservoir holders 412 could be designed for operation with a given type of plug feature 410 or given types. For instance, the plug 410 may have different diameters for different types of drugs. Additionally, different holders 412 may have different configurations of features 414 for removing the plug feature 410.

Since the plug feature 410 is automatically removed the first time the reservoir or cartridge 400 is inserted in a holder 412, the lack of a plug feature 410 may indicate to a user of a reservoir or cartridge 400 that a reservoir or cartridge 400 has been previously used or tampered with. In an example, the cartridge 400 or box may have a warning that if there is no plug 410 and this is the first use of the cartridge 400, the cartridge 400 should not be used.

In another embodiment, a drug reservoir or reservoir assembly may have a tear-away feature 502, 506 (in FIG. 5) disposed on the proximal end 508 and/or the distal end 504, which can be removed by a user before device assembly and may prevent access to the proximal end 508 and/or the distal end 504. In particular, the tear-away feature 502, 506 may prevent the attachment of a dispense interface (e.g., a needle assembly) at the distal end 504, or may prevent access to the cartridge bung or stopper 128.

Figure 5:
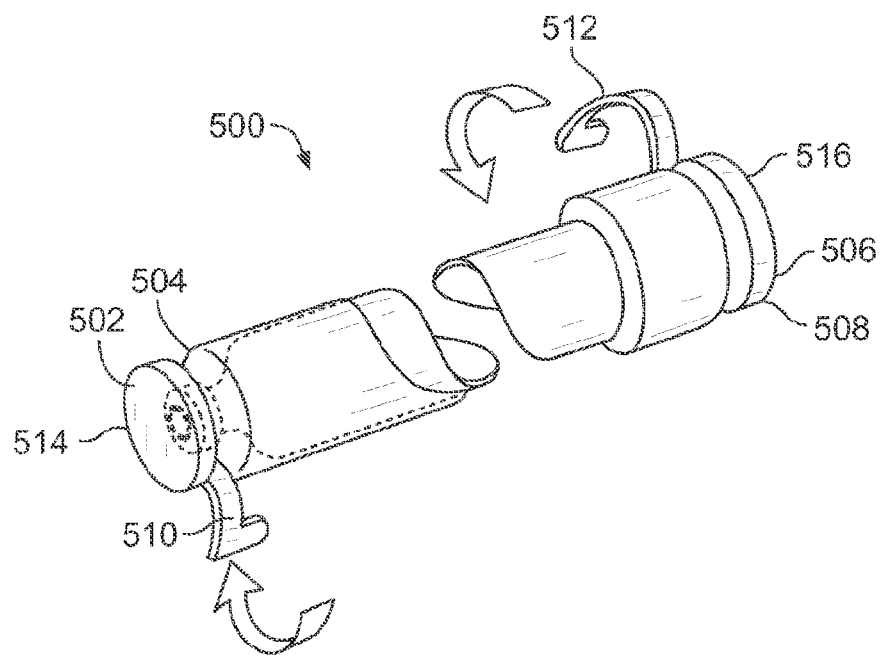
FIG. 5 is yet another example drug reservoir in accordance with an embodiment of the proposed concept.

FIG. 5 depicts a cartridge 500 that includes a tear-away feature 502 on the distal end 504 and a tear-away feature 506 on the proximal end 508. Alternatively, the cartridge 500 may comprise a tear-away feature 502, 506 on at least one of the distal end 504 and the proximal end 508. The tear-away features 502 and 506 include tear-away strips 510 and 512, respectively, and caps 514 and 516, respectively. Cap 514 prevents access to the distal end 504 so that a dispense interface cannot be attached. Cap 516 prevents access to the proximal end 508, so that the bung or stopper 128 cannot be reached (and therefore the medicament 125 cannot be dispensed form the cartridge 500). When the tear-away strip 510, 512 is torn, the caps 514, 516 may fall from the cartridge 500, and the cartridge 500 may then be used for drug delivery. These tear-away features 502, 506 may indicate to the user that the drug has been tampered with by removal of the tamper-evident collar from the cartridge 500 or cartridge assembly.

Although aimed primarily at the insulin market, the presently proposed tamper-evident indicator schemes may apply to other drugs. The coding system may apply to various devices, including the following examples:

An injector pen with a cartridge 120, 200, 300, 400, 500 (e.g. 3 ml cylindrical glass cartridge) and a separate cartridge assembly and/or cartridge holder 104, 412.

An injector pen with a cartridge 120, 200, 300, 400, 500 (e.g. 3 ml cylindrical glass cartridge) non-removably retained in a cartridge assembly and/or cartridge holder 104, 412, so that the assembly will be disposed of with the primary pack.

An injector pen where the primary pack attaches directly to the pen, e.g. an injection-moulded polymer cartridge.

Any drug delivery device 100, with any type of primary pack, e.g. inhaler, pouch.

Figure 6:
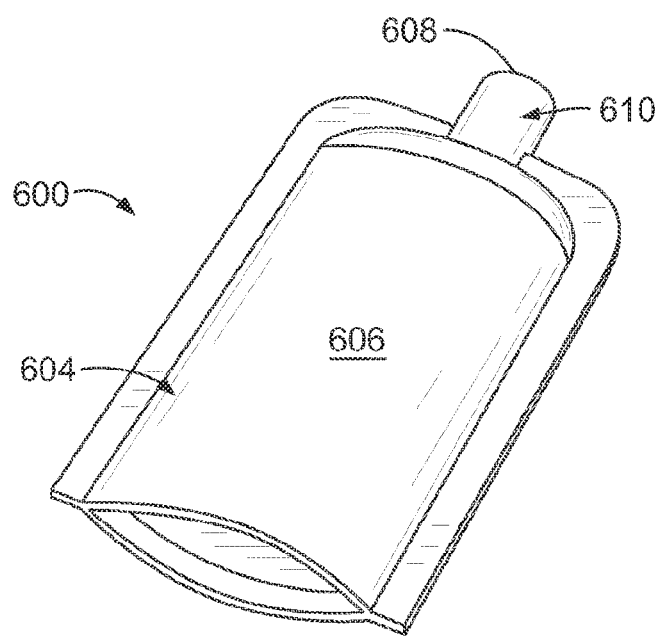
FIG. 6 is a perspective view of an exemplary embodiment of the drug reservoir that may be coded in accordance with the proposed concept.

An example primary pack is shown in FIG. 6. FIG. 6 illustrates a drug reservoir 600 comprising a vessel 604 that contains a medicament 606. A stopper 608 is provided along a distal end of the vessel 604 and is attached to the vessel 604 so as to prevent the medicament 606 from exiting the vessel 604. The coding described above may be provided on the output port 610 of the vessel 604.

Further, although the proposed tamper-evident indicator has been described with reference mainly to a cartridge 120, 200, 300, 400, 500 or cartridge assembly, the proposed system may apply to any location on any components of a drug delivery system 100. For instance, the tamper-evident indicator may apply in the following examples:

a. The interface between a cartridge 120, 200, 300, 400, 500 (or a feature attached to the cartridge 120, 200, 300, 400, 500) and its holder 104, 412;

b. The interface between a cartridge 120, 200, 300, 400, 500 (or a feature attached to the cartridge 120, 200, 300, 400, 500) and the drug delivery device 100; and c. The interface between a cartridge assembly, a molded cartridge assembly, or other primary pack and the drug delivery device 100.

The proposed tamper-evident indicator results in a number of advantages. For example, as discussed above, the tamper-evident indicator may provide an indication to the user that a cartridge 120, 200, 300, 400, 500 or cartridge assembly has been previously used, and thus it may not be advisable to use the given cartridge 120, 200, 300, 400, 500, unless the user is aware of the nature of the previous use of the cartridge 120, 200, 300, 400, 500. Further, the tamper-evident indicator may prevent access to or delivery of a drug without removal of the tamper-evident feature.

Exemplary embodiments have been described. However, as those of skill in the art will recognize certain changes or modifications to such arrangements may be made. As just one example, features discussed herein may be taken from one arrangement and combined with features of other arrangements. Those skilled in the art will understand, however, that further changes, modifications, revisions and/or additions may be made to the presently disclosed arrangements without departing from the true scope and spirit of the present invention, which is defined by the claims.

The invention claimed is:

1. A drug reservoir comprising:
a housing having a proximal end and a distal end, wherein the housing is configured to hold a medicament;
a mechanical coding feature located on either the distal end or the proximal end, wherein the mechanical coding feature is configured to cooperatively engage a complementary corresponding mechanical coding feature located on a given reservoir holder intended for use with the drug reservoir or to cooperatively engage a corresponding mechanical coding feature of a given drug delivery device intended for use with the drug reservoir;

i) wherein the coding feature comprises one or more elongated protrusions and the corresponding mechanical coding feature includes one or more elongated indentations to accommodate the one or more elongated protrusions, or ii) wherein the coding feature includes one or more elongated indentations and the corresponding coding feature includes one or more elongated protrusions coded to the one or more elongated indentations of the coding feature, wherein the one or more elongated protrusions and the one or more elongated indentations are provided on an outside surface of the housing extend along a longitudinal direction that extends from the proximal end towards the distal end; and a removable tear-away feature that acts as a tamper-evident feature, and wherein the tamper-evident feature at least partially covers the mechanical coding feature to prevent use of the drug reservoir with a drug delivery device.

2. The drug reservoir of claim 1, wherein the distal end comprises an opening and a septum, wherein the tear-away feature covers the opening and the septum.

3. The drug reservoir of claim 1, wherein the tear-away feature is a tear-away label or a tear-away strip.

4. The drug reservoir of claim 1, wherein the tear-away feature comprises at least one of foil, vinyl, polyester, and acetate.

5. The drug reservoir of claim 1, further comprising a colored element, wherein the tear-away feature covers the colored element, and wherein the colored element comprises a color that serves to indicate information about the drug reservoir.

6. The drug reservoir of claim 1, further comprising a fastening feature, wherein the tear-away feature is disposed over the fastening feature.

* * * * *